United States Patent [19]

Pugach et al.

[11] Patent Number: 5,075,496

[45] Date of Patent: Dec. 24, 1991

[54] MANUFACTURE OF 2,6-HYDROXYNAPHTHOIC ACID

[75] Inventors: Joseph Pugach, Monroeville Borough, Pa.; Donald T. Derussy, Reynoldsburg, Ohio

[73] Assignee: Aristech Chemical Corporation, Pittsburgh, Pa.

[21] Appl. No.: 629,326

[22] Filed: Dec. 14, 1990

[51] Int. Cl.$^5$ .............................................. C07C 51/15
[52] U.S. Cl. .................................................... 562/425
[58] Field of Search ........................................ 562/425

[56] References Cited

U.S. PATENT DOCUMENTS

| | | | |
|---|---|---|---|
| 1,593,816 | 7/1926 | Andre. | |
| 1,941,207 | 12/1933 | Harvey | 562/425 |
| 2,807,643 | 9/1957 | Harley | 260/520 |
| 2,824,892 | 2/1958 | Barkley | 260/521 |
| 3,655,744 | 4/1972 | Yasuhara et al. | 260/521 R |
| 4,032,568 | 6/1977 | Quadbeck-Seeger | 562/425 |
| 4,057,576 | 11/1977 | Bachmann et al. | 562/425 |
| 4,239,913 | 12/1980 | Ueno et al. | 562/425 |
| 4,287,357 | 9/1981 | Mueller et al. | 562/425 |
| 4,297,508 | 10/1981 | Maegawa et al. | 562/425 |
| 4,329,494 | 5/1982 | Montgomery | 562/425 |
| 4,345,094 | 8/1982 | Mueller | 182/425 |
| 4,345,095 | 8/1982 | Mueller | 562/425 |
| 4,508,920 | 4/1985 | Stopp et al. | 562/423 |
| 4,618,701 | 10/1986 | Neeb et al. | 560/139 |
| 4,780,567 | 10/1988 | Ueno | 562/425 |
| 4,966,992 | 10/1990 | Ueno | 562/425 |
| 5,011,984 | 4/1991 | Ueno | 562/425 |

FOREIGN PATENT DOCUMENTS

| | | |
|---|---|---|
| 1185264 | 4/1985 | Canada. |
| 1190245 | 7/1985 | Canada. |
| 327221 | 9/1989 | European Pat. Off. . |
| 1316343 | 2/1989 | Japan. |

Primary Examiner—Paul J. Killos
Attorney, Agent, or Firm—William L. Krayer

[57] ABSTRACT 2,6-hydroxynaphthoic acid is made by reacting 2-naphthol with cesium or rubidium hydroxide to obtain cesium or rubidium naphthoxide, and reacting the naphthoxide with $CO_2$ in the presence of cesium or rubidium carbonate.

9 Claims, No Drawings

MANUFACTURE OF 2,6-HYDROXYNAPHTHOIC ACID

TECHNICAL FIELD

This invention relates to the production of 2,6-hydroxynaphthoic acid (2,6-HNA) beginning with 2-naphthol. In particular, it relates to the use of cesium or rubidium to replace the hydroxyl proton of the 2-naphthol and then reacting the cesium or rubidium naphthoxide with carbon dioxide in the presence of cesium or rubidium carbonate. Preferred conditions include recommended solvents and pressure ranges.

BACKGROUND OF THE INVENTION

Prior to the present invention it has been known to convert 2-naphthol to 2,3-hydroxynaphthoic acid (2,3-HNA) by reacting the 2-naphthol with sodium hydroxide and then carboxylating the resulting sodium naphthoxide with carbon dioxide. It has also been known that the carboxylation tends to shift to the 6-position if potassium is used instead of sodium. Temperatures also appear to affect the formation of 2,6-HNA as opposed to 2,3-HNA.

After carboxylation, the proton at the carboxylation site is lost and is picked up by a second 2-naphthoxide molecule. Thus, for every mole of product formed, a mole of starting material is formed. This means the best possible conversion is 50%. Addition of potassium carbonate during the second step improves conversion. The products 2,6-HNA, 2,3-HNA and 2-naphthol can be separated by modifying the pH of an aqueous solution containing the three. Typically, 2,6-HNA can be isolated in this manner with 97-99% purity, with 2,3-HNA being the major impurity. It is important to adjust pH precisely and accurately as this can affect the yield and purity of the desired product.

The patent literature contains two processes for the carboxylation of potassium 2-naphthoxide. In one process, a flow of carbon dioxide is passed continuously through the apparatus during carboxylation, claiming a higher yield than in the process without continuous $CO_2$ flow.

SUMMARY OF THE INVENTION

We have found that surprisingly improved results toward, particularly, conversion to 2,6-HNA are achieved in a cesium or rubidium system as compared to a potassium system. Our process for the manufacture of 2,6-HNA involves the reaction of 2-naphthol with cesium or rubidium hydroxide to form cesium or rubidium naphthoxide, and reacting the cesium or rubidium naphthoxide with carbon dioxide in the presence of cesium or rubidium carbonate, at a temperature of about 220° to about 300° C., a pressure of about 20 to about 100 psig, and in a solvent (carrier) medium of a high boiling hydrocarbon, i.e. a linear or cyclic hydrocarbon having about 10 to about 25 carbon atoms.

DETAILED DESCRIPTION OF THE INVENTION

We have found that a dramatic increase in yield of 2,6-HNA can be obtained with our process as compared to processes of the prior art. Selectivities in particular are considerably improved as compared to analogous potassium reactions which our investigations indicated were representative of the best prior art.

Our invention comprises a three-step process:

(1) 2-naphthol is neutralized with cesium or rubidium hydroxide;

(2) the resulting cesium or rubidium naphthoxide product is dried by any convenient method; and (3) the cesium or rubidium naphthoxide is reacted with carbon dioxide in the presence of about 5 to about 60% cesium or rubidium carbonate at temperatures in the range about 220° to about 300° C. and pressures about 20 to about 100 psig in a suitable carrier, for a period of about 4 to about 10 hours.

Our invention is illustrated and compared to the prior art in the examples below.

Table I presents results using certain variations of the prior art potassium method. Example 8 may be taken as representative. Following is a detailed description of example 8:

In a 300 ml autoclave was placed 2-naphthol (36.04 g, 250 mmol), 87.0% potassium hydroxide (16.13 g, 250 mmol), potassium carbonate (17.28 g, 125 mmol), 15 ml water, and 100 ml tetradecane. The mixture was stirred at room temperature under a slow purge of argon for 1 hour before heating to 250° C. and holding at that temperature for 3 hours, at which time ca. 21 ml water and 5 ml tetradecane had been collected in a knock-out pot. After heating to 265° C., the autoclave was charged with 45 psi carbon dioxide with a flow of 250 ml per minute. Conditions were maintained for 6 hours before depressurizing and cooling to room temperature. The contents of the autoclave were transferred to an erlenmeyer flask and water added until a total volume of ca. 550 ml existed. The reaction mixture was heated at 80°-90° C. for 30 minutes and the organic layer containing 2-naphthol removed. The aqueous layer was acidified to pH 7.0 via addition of 1M $H_2SO_4$ and extracted twice with 350 ml toluene at 80° C. The aqueous phase was cooled to room temperature and further acidified to pH 4.0 by addition of 1M $H_2SO_4$, at which time the 2,6-HNA precipitate was collected by filtration, washed with water and dried. There was isolated 11.84 g (25%) of a tan solid which was 97.6% 2,6-HNA, 2.4% 2,3-HNA by G. C. analysis of the material after silylation with N,N-bis(trimethylsilyl)acetamide. The melting point was about 240°-248° C. Further acidification of the filtrate to pH 2.0 with 1M $H_2SO_4$ gave 1.4 g (3%) of a yellow solid which was 86.3%, 2,3-HNA, 13.7% 2,6-HNA by G. C. analysis. The combined organic phases were extracted with 5% NaOH (3×100 ml) and the combined aqueous extracts acidified to a pH less than 2 by addition of 3M HCl. Filtration, a water wash, and drying gave 21.90 g (61%) of recovered 2-naphthol.

Variations from the example 8 procedure, such as the amount of potassium carbonate, the solvent, time of reaction and pressure, are shown in Table I.

TABLE I

2,6-HNA Production Using Potassium Cation (Prior Art)

| No. | Special Conditions | Solvent | Time | Temp | Press | Conversion | Selectivity (2,6-HNA, 2,3-HNA) |
|---|---|---|---|---|---|---|---|
| 1. | 10% $K_2CO_3$ | IPN[1] | 6 h | 260° C. | 42 psi | 46% | 37%, 13% |
| 2. | 50% $K_2CO_3$ | IPN[1] | 6 h | 265° C. | 45 psi | 38% | 58%, 13% |
| 3. | 10% $K_2CO_3$ | IPN[1] | 8 h | 265° C. | 45 psi | 39% | 56%, 18% |
| 4. | 50% $K_2CO_3$ | Kerosene | 6 h | 265° C. | 45 psi | 28% | 57%, 14% |
| 5. | 50% $K_2CO_3$ | Kerosene | 6 h | 265° C. | 45 psi | 32% | 56%, 12% |
| 6. | 10% $K_2CO_3$ | Kerosene | 6 h | 265° C. | 55 psi | 42% | 40%, 12% |
| 7. | 10% $K_2CO_3$ | TMPI[2] | 6 h | 265° C. | 60–75 psi | 45% | 44%, 27% |
| 8. | 50% $K_2CO_3$ | Tetradecane | 6 h | 265° C. | 45 psi | 39% | 64%[3], 8% |
| 9. | 10% $K_2CO_3$ | Tetradecane | 22 h | 265° C. | 45 psi | 51% | 53%[4], 4% |
| 10. | 10% $K_2CO_3$ | Tetradecane | 8 h | 265° C. | 55 psi | 45% | 58%[5], 9% |
| 11. | 10% $K_2CO_3$ | Hexadecane | 8 h | 265° C. | 65 psi | 40% | 50%[6], 12% |

[1]Isopropylnaphthalene
[2]Trimethylphenylindane
[3]97.6% pure
[4]98.1% pure
[5]97.6% pure
[6]96.2% pure Results of the following examples 12–18 illustrate the improvements obtained by using the cesium or rubidium of our invention, and are shown in Table II.

Cesium Method (Table II, example 12)

Using 2-naphthol (36.04 g, 250 mmol), 74.96 g of 50 wt% aqueous cesium hydroxide (250 mmol), cesium carbonate (8.14 g, 25 mmol) and 95 ml hexadecane gave 16.72 g (36%) 2,6-HNA (G. C. analysis 98.5% 2,6-HNA, 1.5% 2,3-HNA), 1.90 g (4%) 2,3-HNA (G. C. analysis 95.5% 2,3-HNA, 4.5% 2,6-HNA) and 19.09 g (53%) recovered 2-naphthol.

Cesium Method (Table II, Example 13)

Using 2-naphthol (36.04 g, 250 mmol), 74.96 g of 50 wt% aqueous cesium hydroxide (250 mmol), cesium carbonate (8.14 g, 25 mmol) and 95 ml hexadecane gave 17.53 g (37%) 2,6-HNA (G. C. analysis 98.0% 2,6-HNA, 2.0% 2,3-HNA), 1.90 g (4%) 2,3-HNA (G. C. analysis 88.1%, 2,3-HNA, 11.9% 2,6-HNA) and 16.51 g (46%) recovered 2-naphthol.

Cesium Method (Table II, example 14)

Using 2-naphthol (36.04 g, 250 mmol), 74.96 g of 50 wt% aqueous cesium hydroxide (250 mmol), cesium carbonate (8.14 g, 25 mmol), 95 ml hexadecane and a carbon dioxide pressure of 55 psi gave 16.27 g (35%) 2,6-HNA, 1.84 g (4%) 2,3-HNA, both having a similar purity as above and 19.46 g (54%) recovered 2-naphthol.

Cesium Method (Table II, example 15)

Using 2-naphthol (36.04 g, 250 mmol), 74.96 g of 50 wt% aqueous cesium hydroxide (250 mmol), cesium carbonate (8.14 g, 25 mmol), 95 ml hexadecane and a carbon dioxide pressure of 85 psi gave 18.21 g (39%) 2,6-HNA (G. C. analysis 98.8% 2,6-HNA, 1.2% 2,3-HNA), 3.59 g (8%) 2,3-HNA (G. C. analysis 78.0% 2,3-HNA, 12.0% 2,6-HNA) and 15.73 g (44%) recovered 2-naphthol.

Cesium Method Excluding Cesium Carbonate (Table II, example 16)

Processing 2-naphthol (36.04 g, 250 mmol), 74.96 g of 50 wt% aqueous cesium hydroxide (250 mmol), and 95 ml hexadecane yielded 11.23 g (24%) 2,6-HNA (G. C. analysis 97.4% 2,6-HNA, 2.6% 2,3-HNA), 2.07 g (4%) 2,3-HNA (G. C. analysis 87.5% 2,3-HNA, 12.5% 2,6-HNA) and 23.10 g (64%) recovered 2-naphthol.

Mixture 90% Potassium and 10% Cesium (Table II, example 17)

With 2-naphthol (36.04 g, 250 mmol), 7.50 g of 50 wt% aqueous cesium hydroxide (25 mmol), 87.9% potassium hydroxide (14.02 g, 225 mmol), potassium carbonate (3.46 g, 25 mmol), 15 ml water, and 95 ml hexadecane, the usual reaction produced 10.66 g (23%) 2,6-HNA (G. C. analysis 96.6% 2,6-HNA, 3.4% 2,3-HNA), 3.00 g (6%) 2,3-HNA (G. C. analysis 84.6%, 2,3-HNA, 15.4% 2,6-HNA) and 19.13 g (53%) recovered 2-naphthol.

Rubidium Method (Table II, example 18)

Using 2-naphthol (36.04 g, 250 mmol), 51.24 g of 50 wt% aqueous rubidium hydroxide (250 mmol), rubidium carbonate (5.77 g, 25 mmol) and 95 ml hexadecane, there was obtained 16.53 g (35%) 2,6-HNA, 1.82 g (4%) 2,3-HNA, both having a similar purity as above and 20.98 g (58%) recovered 2-naphthol.

TABLE II

2,6-HNA Production Using Cesium[1] or Rubidium Cation[2]

| No. | Special Conditions | Solvent | Time | Temp | Press | Conversion | Selectivity (2,6-HNA, 2,3-HNA) |
|---|---|---|---|---|---|---|---|
| 12. | 10% | Hexa- | 6 h | 265° C. | 45 psi | 47% | 76%[3], 8% |

TABLE II-continued 2,6-HNA Production Using Cesium[1] or Rubidium Cation[2]

| No. | Special Conditions | Solvent | Time | Temp | Press | Conversion | Selectivity (2,6-HNA, 2,3-HNA) |
|---|---|---|---|---|---|---|---|
| 13. | $Cs_2CO_3$ 10% $Cs_2CO_3$ | decane Hexadecane | 6 h | 265° C. | 45 psi | 54% | 68%[4], 7% |
| 14. | 10% $Cs_2CO_3$ | Hexadecane | 6 h | 265° C. | 55 psi | 46% | 76%, 9% |
| 15. | 10% $Cs_2CO_3$ | Hexadecane | 6 h | 265° C. | 85 psi | 56% | 70%, 14% |
| 16. | no $Cs_2CO_3$ | Hexadecane | 6 h | 265° C. | 45 psi | 36% | 67%, 11% |
| 17. | 90% K+, 10% Cs+ | Hexadecane | 6 h | 265° C. | 45 psi | 47% | 49%, 13% |
| 18. | 10% $Rb_2CO_3$ | Hexadecane | 6 h | 265° C. | 45 psi | 42% | 83%, 10% |

[1] Examples 12-17.
[2] Example 18.
[3] 98.5% pure
[4] 98.0% pure

As can be seen, the 2,6-HNA selectivity was much improved with cesium over the analogous potassium reaction, accompanied by a small increase in conversion (compare Table I, example 8 with Table II, example 12). The result was an approximate 44% increase in isolated yield of 2,6-HNA.

A few variables were tested with the cesium examples. First, an increase in carbon dioxide pressure to 85 psi doubled 2,3-HNA selectivity (compare example 15 with examples 12 and 13). Next, a reaction excluding cesium carbonate gave conversion and selectivity numbers similar to the potassium reactions. The presence of cesium or rubidium carbonate appears to be essential (in the range of about 5% to about 60% of the naphthol salt) for maximized conversion and selectivity. The possibility that only a small amount of cesium would give increased conversion and selectivity was dispelled in example 17. As can be seen in example 18, an increase in conversion and the best selectivity was found with rubidium.

We claim:

1. Method of making 2,6-hydroxynaphthoic acid comprising (a) reacting 2-naphthol with a hydroxide of an alkali metal selected from the group consisting of cesium and rubidium to obtain an alkali metal naphthoxide, (b) drying the resulting alkali metal naphthoxide, and (c) reacting the alkali metal naphthoxide with carbon dioxide at a pressure of about 20 to about 100 psig in the presence of a high boiling hydrocarbon solvent and a carbonate of an alkali metal selected from the group consisting of cesium and rubidium.

2. Method of claim 1 wherein the alkali metal carbonate in step (c) is present in an amount from about 5 to about 60% of the alkali metal naphthoxide.

3. Method of claim 1 wherein the solvent in step (c) is selected from linear and cyclic hydrocarbons having from about 10 to about 25 carbon atoms.

4. Method of claim 1 wherein the alkali metal in steps (a) and (c) is cesium.

5. Method of claim 1 wherein the alkali metal in steps (a) and (c) is rubidium.

6. Method of claim 1, wherein the pressure in step (c) is about 20 to about 100 psig.

7. Method of claim 1 wherein the solvent is hexadecane.

8. Method of claim 1 followed by the step of separating 2,6-hydroxynaphthoic acid from the reaction mixture.

9. Method of claim 1 wherein step (c) is conducted at a temperature between about 220° C. and about 300° C.

* * * * *